United States Patent [19]

Karapetian et al.

[11] 4,434,796
[45] Mar. 6, 1984

[54] SURGICAL STAPLE, A METHOD OF AND FORCEPS FOR ITS REMOVAL

[75] Inventors: Igor S. Karapetian; Ivan A. Korolkov; Nikolai N. Kapitanov; Boris A. Smirnov; Tatyana L. Ivanova, all of Moscow, U.S.S.R.

[73] Assignee: Vsesojuzny Nauchno-Issledovatelsky I Ispytatelny Institut Meditsinskoi Tekhniki, Moscow, U.S.S.R.

[21] Appl. No.: 350,398

[22] Filed: Feb. 19, 1982

[30] Foreign Application Priority Data

Apr. 7, 1981 [SU] U.S.S.R. ............................... 3275314

[51] Int. Cl.³ ............................................. A61B 17/08
[52] U.S. Cl. ................................... 128/335; 128/92 B
[58] Field of Search ............ 128/334 R, 334 C, 92 R, 128/92 B, 92 BA, 92 D, 335, 337

[56] References Cited

U.S. PATENT DOCUMENTS

| 324,768 | 8/1885 | Hunt | 128/92 B |
| 2,631,584 | 3/1953 | Purificato | 128/92 BA |
| 3,825,010 | 7/1974 | McDonald | 128/335 X |

*Primary Examiner*—John D. Yasko
*Attorney, Agent, or Firm*—Murray Schaffer

[57] ABSTRACT

The staple has two legs interconnected through a web. Each of the legs carries a rod having a pointed bottom end and a head. The head has a slot for the web to pass. A through hole or passage is made in the rod, which is open at the slot in the head and at the side rod surface. The rigidity of the leg decreases from the zone of interconnection with the web towards the leg end. A method of and forceps for removal of such a surgical staple are also disclosed.

4 Claims, 8 Drawing Figures

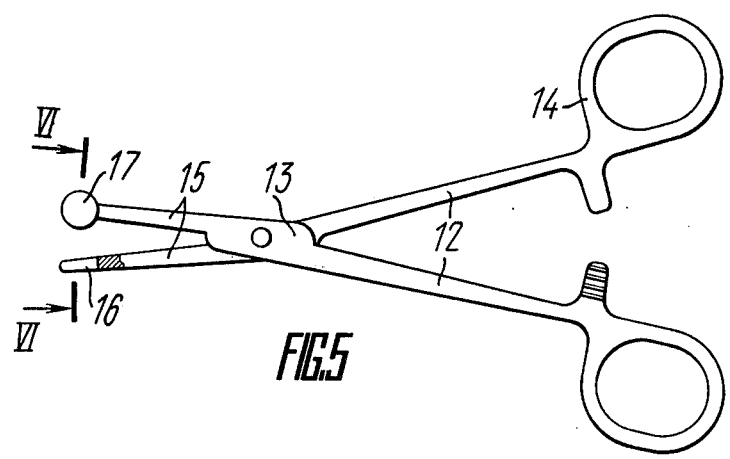
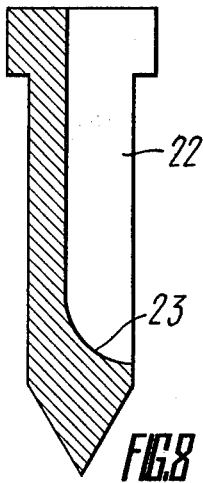
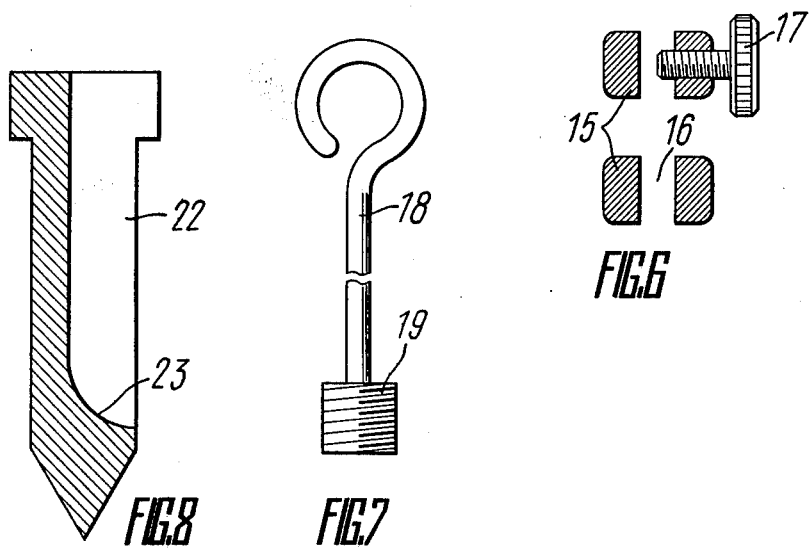

SURGICAL STAPLE, A METHOD OF AND FORCEPS FOR ITS REMOVAL

The present invention relates generally to medical equipment and has particular reference to a surgical staple adapted for uniting some tissues by a staple suture, especially for uniting the bone tissue.

One prior-art surgical staple is known to comprise two legs having longitudinal recesses and interconnected by a web (cf., e.g. USSR Inventor's Certificate No. 227,506 issued in 1967).

The aforesaid staple fails to be bent inside the tissue operated upon nor can it be withdrawn upon knitting consolidation of the bone tissue involved, whenever it becomes necessary in cases of inflammatory reactions of the bone.

The staple legs are bent manually under the bone being sutured.

It is a primary object of the present invention to provide a surgical staple that could be easy-to-bend immediately inside the bulk of an organ (bone) by virtue of self-bending.

It is another object of the present invention to provide a surgical staple that could be introduced with a lower degree of traumatism.

It is more object of the present invention to provide a surgical suture that could be easy-to-remove.

Among the other objects of the present invention worth noting is the provision of a special method of and device for removal of such a staple.

Said and other objects are accomplished due to the fact that in a surgical staple, comprising two legs interconnected by a web, according to the present invention, each of the legs carries a rod with a pointed bottom end and a head having a slot for the staple web to pass, while a through hole or passage is made in the rod, which is open at the slot in the head and at the side surface of the rod cylindrical portion, and the rigidity of the leg decreases from the place of its interconnection with the web towards its end.

An advantageous feature of such a staple resides in its self-retaining in the bone tissue operated upon. Since the staple legs feature variable rigidity their bending and penetration into the bone tissue occur smoothly and require a relatively low force, whereby the operation for suturing the bone fragments becomes less traumatic and painful.

Moreover, the herein-disclosed surgical staple is advantageous over all the heretofore-used ones adapted for uniting various tissues in being withdrawable after the bone fragments have knitted. This may become necessary in some medical indications, e.g., in cases of osteomyelitis.

It is expedient that one of the embodiments of the present invention makes provision for an axial slot in the rod, which is open at the side rod surface and has a rounded-off portion at its bottom end.

According to the present invention, prior to removing the surgical staple in question one must nip up the staple web, whereupon one of the forceps jaws is placed on the rod head and the staple leg is stationary fixed to the other jaw, and the forceps jaws are brought apart.

Provision is also made in the forceps for a clamp for the staple leg to fix.

An advantageous feature of such a method consists in a possibility of employing a relatively simple device, e.g., a forceps when but slightly modified.

In what follows the present invention will be illustrated in a detailed description of some specific embodiments thereof which are by no means limitative upon the present invention, and the accompanying drawings, wherein:

FIG. 5 is a view of the staple extracting forceps;

FIG. 6 is a section through the forceps jaws taken along the line VI—VI in FIG. 5;

FIG. 7 is a view of the rod extractor; and

FIG. 8 is a view of the rod having a hole open at its side surface.

Figure 1:
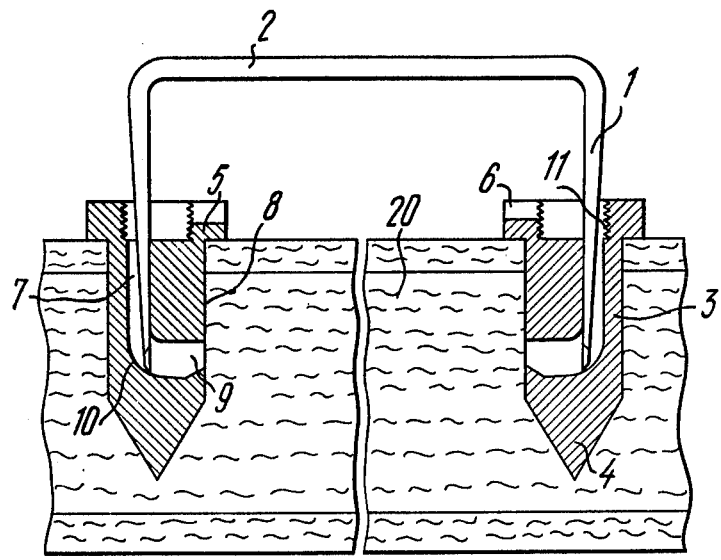
FIG. 1 is a sectional view of the surgical staple in question, illustrating the rods having forced their way into the bone tissue and the staple legs still remaining not bent.
Figure 2:
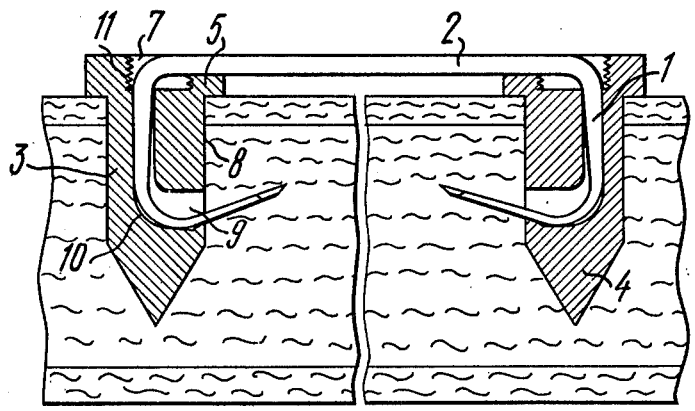
FIG. 2 is a sectional view of the surgical staple in question, illustrating the staple legs having got bent and forced their way into the bone tissue.

Referring now to FIGS. 1 and 2 illustrating a surgical staple, said staple comprises two legs 1 interconnected by a web 2. For a smoother bending and lower bending force the staple leg 1 grows thinner from the place of its interconnection with the web 2 towards the end as can distinctly be seen in the drawing.

Each of the legs 1 of the surgical staple carries a rod 3 having a pointed bottom end 4 and a head 5, which has a radial slot 6 for the staple web 2 to pass.

An axial hole or passage 7 is provided in the rod, said hole being open at the slot 6 in the head 5, while a radial hole 9 is made in a side surface 8 of the cylindrical rod portion, said hole being open at said side surface, the zone of transition of the axial hole 7 into the radial hole 9 having a rounded-off portion 10.

A thread 11 is provided in the hole 7 on the side of the rod head 5.

A surgical staple is inserted as follows (FIG. 2). Using a surgical suturing instrument or any other device suitable for the purpose (not shown) one of the rods 3 is made to penetrate into one of the bone fragments, whereas the other rod is driven into the other bone fragment, whereupon a force is applied to the staple web 2. As a result the staple is acted upon by said force to move towards the rods, the staple legs 1 thrust against the rounded-off portion 10 to get bent and to penetrate into the bone tissue, thus strongly uniting the bone fragments, while the web 2 is accommodated in the slot 6.

In cases of osteomyelitis (inflammation of osseous tissue) any alien body must be extracted from the bone tissue. However, none of the now-existing surgical staples can be withdrawn from the bone tissue operated upon.

The herein-disclosed surgical staple can easily be removed from the bone tissue after the bone fragments have knitted by making resort to the instruments now in common use in, say, the following way. The staple web is nipped up with a medical (dental) cutting forceps. Then each of the legs is gripped individually by a medical forceps, e.g., Kocher's, and first pulled out is the staple, then the rod. However, such a method of removing the staple of the present invention might be rather painful for the patient. That is why a special relatively simple device has been developed by us for removing the staple according to the present invention. The device is based on a slightly modified heretofore applicable forceps which is shown in FIG. 5. The forceps comprises arms 12, a lock 13, ring-shaped handles 14 and jaws 15 having slots 16 (FIG. 6). One of the jaws 15 carries a locking screw 17.

A special extractor (FIG. 7) has been developed for withdrawing the rod according to the present invention, said extractor being essentially a shank 18 having a thread 19 at its one end.

Figure 3:
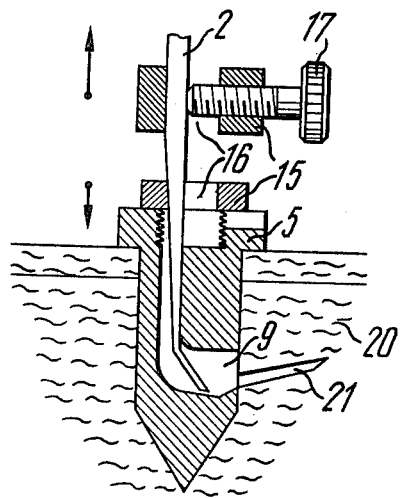
FIG. 3 is a fragmentary view of the staple when being withdrawn from the bone tissue.
Figure 4:
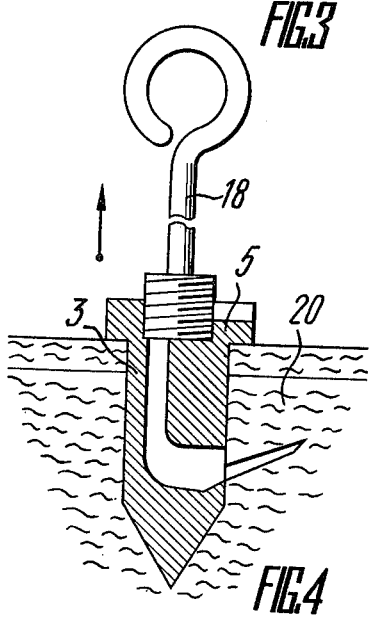
FIG. 4 is a fragmentary view of the staple when the rod is being removed from the bone tissue.

To remove the herein-disclosed device, the soft cover tissues are slit open to expose the staple web 2 and the rod heads 5. Then the staple web is nipped up with a medical (dental) cutting forceps, the staple leg 1 is gripped by the forceps jaws 15 (FIG. 3) in such a manner that the leg should enter the slots 16 in the forceps jaws 15, and is clamped by the locking screw 17. The jaw 15 devoid of the locking screw 17 rests against the rod head 5, whereby the jaws 15 get open. As a result, the staple leg 1 comes out of a bone tissue 20 and on passing through the radial portion 9 of the hole in the rod is straightened and then pulled out of the rod. A hollow 21 is left in the bone tissue 20 after extracting the staple leg 1 therefrom, which is rather fast to heal up.

Then the threaded end of the extractor shank 18 is turned into the threaded portion 11 of the rod, and the latter is pulled out of the bone tissue. The hollow left by the rod is likewise liable to heal up fast.

According to another constructional arrangement of the rod (FIG. 8) a hole 22 in the rod is open at the rod side surface and has a rounded-off portion 23 at the rod bottom end.

Though the present invention has been described in connection with optimum embodiments thereof, it should however be understood by those skilled in the art that a great many modifications and changes may be made without departing from the spirit and scope of the invention as defined in the claims to follow.

What we claim is:

1. A surgical staple, comprising two legs, a web interconnecting said two legs, pointed-end rods adapted to be fitted on each of the staple legs, each of said rods having a head with a slot for said web to pass, a through hole or passage in said rod for the respective staple leg to pass, said hole being open at said slot in said head and at the side surface of said rod, while the rigidity of said staple legs decreases from the zone of their interconnection with the web towards their end.

2. A surgical staple as claimed in claim 1, wherein said through hole in the rod has an axial portion passing lengthwise the rod and open at the rod head, and a radial portion interconnected with said axial portion and open at the side rod surface, the axial portion-to-radial portion transition zone featuring a rounded-off pattern.

3. A surgical staple as claimed in claim 1, wherein the hole in the rod is made as an axial slot open at the side rod surface and having a rounded-off portion at the bottom end thereof.

4. A surgical staple as claimed in claim 1, wherein the staple leg grows thinner from the place of its interconnection with the web towards its end.

* * * * *